United States Patent
Baker et al.

(10) Patent No.: US 8,015,136 B1
(45) Date of Patent: Sep. 6, 2011

(54) ALGORITHMIC METHOD FOR GENERATING A MEDICAL UTILIZATION PROFILE FOR A PATIENT AND TO BE USED FOR MEDICAL RISK ANALYSIS DECISIONING

(75) Inventors: Jay Baker, Foothill Ranch, CA (US); Reza M B'Far, Huntington Beach, CA (US)

(73) Assignee: Dynamic Healthcare Systems, Inc., Irvine, CA (US)

( * ) Notice: Subject to any disclaimer, the term of this patent is extended or adjusted under 35 U.S.C. 154(b) by 768 days.

(21) Appl. No.: 12/080,497

(22) Filed: Apr. 3, 2008

(51) Int. Cl.
*G06F 17/00* (2006.01)
(52) U.S. Cl. .......................................................... 706/45
(58) Field of Classification Search .................. 706/12, 706/45–48, 52
See application file for complete search history.

(56) References Cited

U.S. PATENT DOCUMENTS

| | | | |
|---|---|---|---|
| 5,970,463 A | 10/1999 | Cave et al. | |
| 6,223,164 B1 | 4/2001 | Seare et al. | |
| 6,266,645 B1 | 7/2001 | Simpson | |
| 6,370,511 B1 | 4/2002 | Dang | |
| 6,802,810 B2 | 10/2004 | Ciarniello et al. | |
| 7,127,407 B1 | 10/2006 | Averill et al. | |
| 7,209,923 B1 | 4/2007 | Cooper | |
| 7,222,079 B1 | 5/2007 | Seare et al. | |
| 2006/0020466 A1 | 1/2006 | Cousineau et al. | |
| 2006/0052945 A1 | 3/2006 | Rabinowitz et al. | |
| 2006/0074712 A1 | 4/2006 | Jorgensen et al. | |
| 2007/0094188 A1* | 4/2007 | Pandya et al. | 706/45 |
| 2007/0130206 A1 | 6/2007 | Zhou et al. | |
| 2008/0059391 A1* | 3/2008 | Rosales et al. | 706/12 |
| 2008/0077548 A1* | 3/2008 | Michelin | 706/50 |
| 2008/0201280 A1* | 8/2008 | Martin et al. | 706/12 |
| 2009/0248734 A1* | 10/2009 | Adelman et al. | 707/103 R |

* cited by examiner

*Primary Examiner* — David R Vincent
(74) *Attorney, Agent, or Firm* — Thomas I. Rozsa

(57) ABSTRACT

An algorithmic method for generating a medical utilization profile for a patient to facilitate decision making in the medical risk analyses, wherein the algorithmic method is comprised of four key components: (1) key independent variables recognized including medical data sources; (2) an ontology based process to organize these variables; (3) rules (probability distributions etc.) that can be used to draw correlative information from the given data and its ontological organization; and (4) usage of reasoning engine to process the gathered information and draw inferences.

20 Claims, 3 Drawing Sheets

Activity Diagram of a Possible Realization of the Algorithmic Invention

Activity Diagram of a Possible Realization of the Algorithmic Invention

Architectural Technology Stack Implementation

Base ontology model created as an application of the algorithm to the example problem.

ALGORITHMIC METHOD FOR GENERATING A MEDICAL UTILIZATION PROFILE FOR A PATIENT AND TO BE USED FOR MEDICAL RISK ANALYSIS DECISIONING

BACKGROUND OF THE INVENTION

1. Field of the Invention

The present invention is related to decision making for cost effectiveness in medical treatment, and more particularly related to an algorithmic method for generating a medical utilization profile for a patient to thereby facilitate medical risk decisioning.

2. Description of the Prior Art

The following 12 patents and published patent applications are the closest prior art references which are related to the present invention.

1. U.S. Pat. No. 5,970,463 issued to Douglas G. Cave et al. and assigned to Practice Patterns Science, Inc. on Oct. 19, 1999 for "Medical Claims Integration And Data Analysis System" (hereafter the "Cave Patent");
2. U.S. Pat. No. 6,223,164 issued to Jerry G. Seare et al. and assigned to Ingenix, Inc. on Apr. 24, 2001 for "Method And System For Generating Statistically-Based Medical Provider Utilization Profiles" (hereafter the "'164 Seare Patent");
3. U.S. Pat. No. 6,266,645 issued to Kit N. Simpson and assigned to iMetrikus, Inc. on Jul. 24, 2001 for "Risk Adjustment Tools For Analyzing Patient Electronic Discharge Records" (hereafter the "Simpson Patent");
4. U.S. Pat. No. 6,370,511 issued to Dennis K. Dang and assigned to Symmetry Health Data System, Inc. on Apr. 9, 2002 for "Computer-Implemented Method For Profiling Medical Claims" (hereafter the "Dang Patent");
5. U.S. Pat. No. 6,802,810 issued to Anthony Ciarniello et al. and assigned to Active Health Management on Oct. 12, 2004 for "Care Engine" (hereafter the "Ciarniello Patent");
6. United States Published Patent Application No. 2006/0020466 to Leo E. Cousineau et al. on Jan. 26, 2006 for "Ontology Based Medical Patient Evaluation Method For Data Capture And Knowledge Representation" (hereafter the "Cousineau Published Patent Application");
7. United States Published Patent Application No. 2006/0052945 to Matthew Rabinowitz et al. on Mar. 9, 2006 for "System And Method For Improving Clinical Decisions By Aggregating, Validating And Analysing Genetic And Phenotypic Data" (hereafter the "Rabinowitz Published Patent Application");
8. United States Published Patent Application No. 2006/0074712 to Kelly R. Jorgensen et al. on Apr. 6, 2006 for "Systems And Methods For Supplying A Useful Collection Of Medical Coding Data" (hereafter the "Jorgensen Published Patent Application");
9. U.S. Pat. No. 7,127,407 issued to Richard Francis Averill et al. and assigned to 3M Innovative Properties Company on Oct. 24, 2006 for "Method Of Grouping And Analyzing Clinical Risks, And System Therefor" (hereafter the "Averill Patent");
10. U.S. Pat. No. 7,209,923 issued to Richard G. Cooper on Apr. 24, 2007 for "Organizing Structured And Unstructured Database Columns Using Corpus Analysis And Context Modeling To Extract Knowledge From Linguistic Phrases In The Database" (hereafter the "Cooper Patent");
11. U.S. Pat. No. 7,222,079 issued to Jerry G. Seare et al. and assigned to Ingenix, Inc. on May 22, 2007 for "Method And System For Generating Statistically-Based Medical Provider Utilization Profiles" (hereafter the "'079 Seare Patent"); and
12. United States Published Patent Application No. 2007/0130206 to Xiang Zhou et al. on Jun. 7, 2007 for "System And Method For Integrating Heterogeneous Biomedical Information" (hereafter the "Zhou Published Patent Application").

The Cave Patent discloses a medical claim integration and data analysis system. Although the invention is focused on application to the medical claims, the invention is also intended to solve problems including: "some of which (claims) have principal diagnosis codes, some of which have non-principal, missing, or incorrect diagnosis codes" (Abstract). In addition, the ICD.9 code is indicated by the Cave Patent as one of the principal diagnosis codes that the invention is targeted on analysis (column 8, line 27, continued to column 9, line 12). For diagnosis of the ICD. 9 code, the invention applies the mapping technique (column 8, lines 43 to 44), which is one of the classification methods to identify interests of study.

There are some very clear differences in the technical approach that Cave takes from the present application algorithm:

1. The Cave Patent abstract states: "A diagnosis cluster lookup table enables claim items to be categorized into PTEs with ongoing treatment windows for which the diagnosis code of the claim item is in the diagnostic cluster look up table". This is actually a completely different approach the present invention. The present invention uses ontologies which, in the context of comparison to lookup tables, can render results much faster (and therefore be more scalable in real-life systems that have massive amounts of data) and can provide non-linear interpolative results for gaps that may exist in the data. The combination of ontologies and reasoners can also be considered self-learning as introduction of additional data can yield new unintended inferences.

2. The independent variables recognized in the Cave Patent are limited to patient treatment information. The present invention algorithm incorporates a wider base of independent variables which can in turn yield a significantly more accurate result.

The Seare Patent is a method and system for generating statistically based medical provider utilization profiles. The invention is to provide a method for comparing profiles, particularly for comparing index codes including the ICD-9 code against historical reference information such as the historical medical provider billings.

The Simpson Patent is a risk adjustment tool for analyzing patient electronic discharge records through a selective extraction procedure. In the procedure, the content of the discharge records is matched against one or more "key explanatory variables" such as a "selection vector" which is a collection of patient codes including the ICD.9 code that implicitly specify the condition of interest.

The Dang Patent is a computer-implemented method for profiling medical claims to assist health care managers in determining the cost-efficiency and service quality to health care providers. The objective is for measuring and qualifying health care service based upon medical episode treatment groups.

The Ciarniello Patent offers a comprehensive solution to care management. The invention offers including (1) application tools for identifying potentially problematic patient cases, (2) case and disease management applications and programs for managing problematic and complex cases and (3) applications and services to improve overall risk underwriting profitability. The invention aggregates, integrates and stores clinical information from disparate sources through providing an example of analysis using a hypothetical patient, Jane (column 6, line 32 continued to column 7, line 12). In the analysis, the Patent discloses that through comparison of her available lab, prescription and claims data, it finds the drug Glucophage which is not recommended. Through this example, it is clear that the Ciarniello Patent does not apply statistical methods in the analysis, as compared with your invention.

The Cousineau Published Patent Application discloses an ontology based medical patient evaluation method for data capture and knowledge representation. It specifically discloses two key processing steps: (1) the syntax and (2) ontology processing step. From application of the invention, non standard input data can be converted into the standardized output data. The Cousineau Patent states: "In one embodiment, the invention provides a patient evaluation method wherein non-standard input data is received in a syntax processing block and a corrected data file is generated in relation to a healthcare lexicon." Therefore, the focus of the Cousineau's Patent is to clean up the input for further processing by some other system.

Nearly all of the other claims of the Cousineau Patent focus on the method of collection of data (such as voice, through a wireless network, etc.) where the ontology techniques are used for organization and clean up of the data. There is no mention of usage of reasoners, application of stochastic, statistic, or other mathematical techniques to help provide a viable risk model, and finally no specification of key independent variables required to construct such model.

The Rabinowitz Published Patent Application is focused on applying statistical methods to aggregate, validate and analyze genetic and phenotypic data for caregivers to make better decisions. The Patent Application discloses including the regression method to statistically treat data (Paragraph [0205]). In addition, from using the statistical Model Expert 301 and 302 "the data can be automatically inhaled into the standardized ontology, and can be acted upon by the published training and mapping functions . . . " (Paragraph [0211]).

The Jorgensen Published Patent Application discloses a system and method for supplying a useful collection of medical coding data, which does not apply the ontology and set theory.

The Averill Patent creates a comprehensive set of risk groups which in particular explicitly identifies groups of individuals with multiple interacting co-morbid conditions, and which explicitly identifies the severity of illness level. The invention includes application of the ICD-9 codes to establish Major Disease Categories (MDCs).

The Cooper Patent illustrates how to apply Corpus analysis to information captured in databases which generates an ontology. It uses case-based methods to automatically organize cases for periodic review.

The Seare Patent is a process for analyzing healthcare providers' billing pattern to assess utilization patterns of medical services. The method of the invention incorporates a set of statistically derived and clinically validated episodes of care data to be used as a paradigm for analyzing and comparing providers' services for specific diagnoses on medical conditions (col. 18, lines 31-37). The comparison of profiles function provides a comparison between any two profiles sources with attention to variance between them. Some examples include comparing a specific subset of the client's data against either reference tables or the client's profiles, or comparing different subsets of the client's profiles to subsets of reference tables (col. 18, lines 54-61).

The Seare Patent provides a method and system for analyzing historical medical provider billings to statistically establish a normative utilization profile. The method and system of this invention may be implemented in conjunction with a general purpose or special purpose computer system. The first point is important as the present invention is not limited to historical data (this is only one of the independent variables we're recognizing in the process of building an ontology). The second is important because the present invention is an algorithmic/technology focus versus a purely historical focus that any technology may use.

The Zhou Published Patent Application is a system and method for integrating heterogeneous biomedical information. The system is dictated by three orthogonal views (Paragraph [0019]). The method includes ontologies which are used to formally express the medical domain for improved communication of domain concepts among domain components, and to assist in the integration process. Mapping discovery is used to identify similarity between ontologies, determining which concepts and properties represent similar notions either automatically or semi-automatically (Paragraph [0020]). Generative and discriminative models can also be used to support tasks such as disease and disease subclass classification, modeling, and predication (Paragraph [0025]). The use of statistical learning algorithms can shift the burden of feature space manipulation from the user to the machine. Small-sample learning algorithms based on Kernel BiasMap and Rankboosting can be a specific choice of such type of statistical learning algorithms (Paragraph [0026]).

Therefore, there is a significant need to provide an algorithmic method which can be used to generate a medical utilization profile for a patient for facilitating decision making in the medical risk analyses.

SUMMARY OF THE INVENTION

The present invention is an algorithmic method for generating a medical utilization profile for a patient to facilitate decision making in the medical risk analyses, wherein the algorithmic method is comprised of four key components: (1) key independent variables recognized including medical data sources; (2) an ontology based process to organize these variables; (3) rules (probability distributions etc.) that can be used to draw correlative information from the given data and its ontological organization; and (4) usage of reasoning engines to process the gathered information and draw inferences.

Specifically, the algorithmic method is comprised of the following step:
(a) determining medical data sources which contain medical data of said patient;
(b) applying reasoning engines to define an initial ontology model which matches said data sources;
(c) creating an ontology implementation that includes characterization, classification of said medical date in a given analysis sequence;
(d) enabling said initial ontology model to thereby modify said initial model; and
(e) comparing the initial ontology model with the modified ontology model through a Set Theory including comparing with intersections and unions which yields results to drive business rules.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Figure 1:
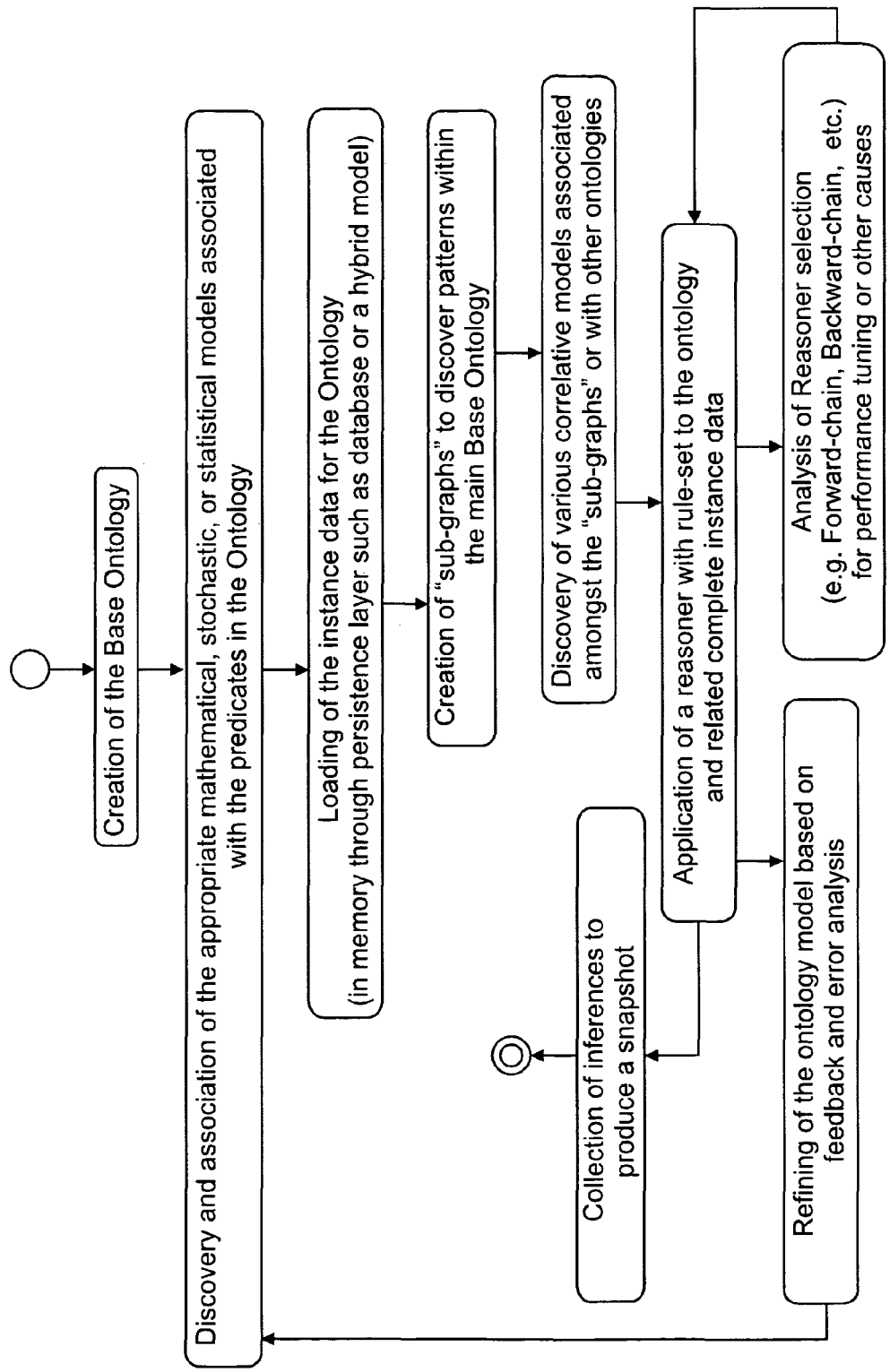
FIG. 1 is an activity diagram of a possible realization of the algorithmic invention.
Figure 2:
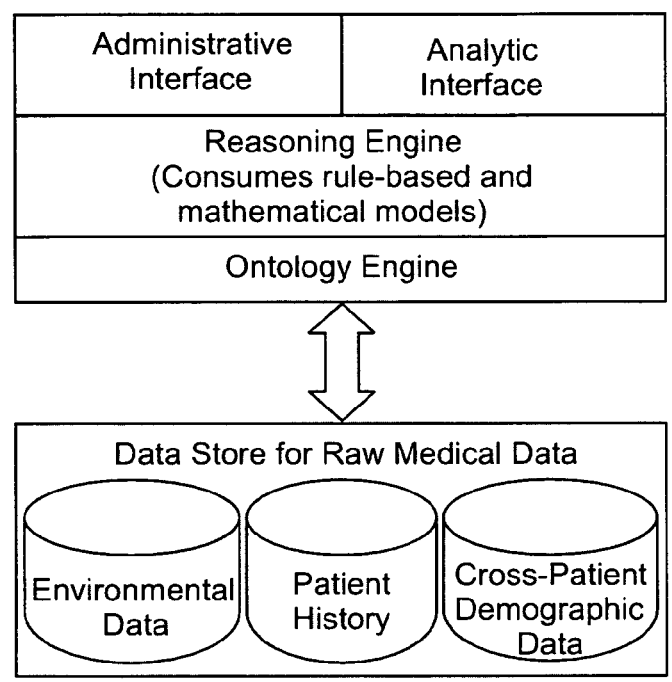
FIG. 2 is an architectural technology stack implementation.
Figure 3:
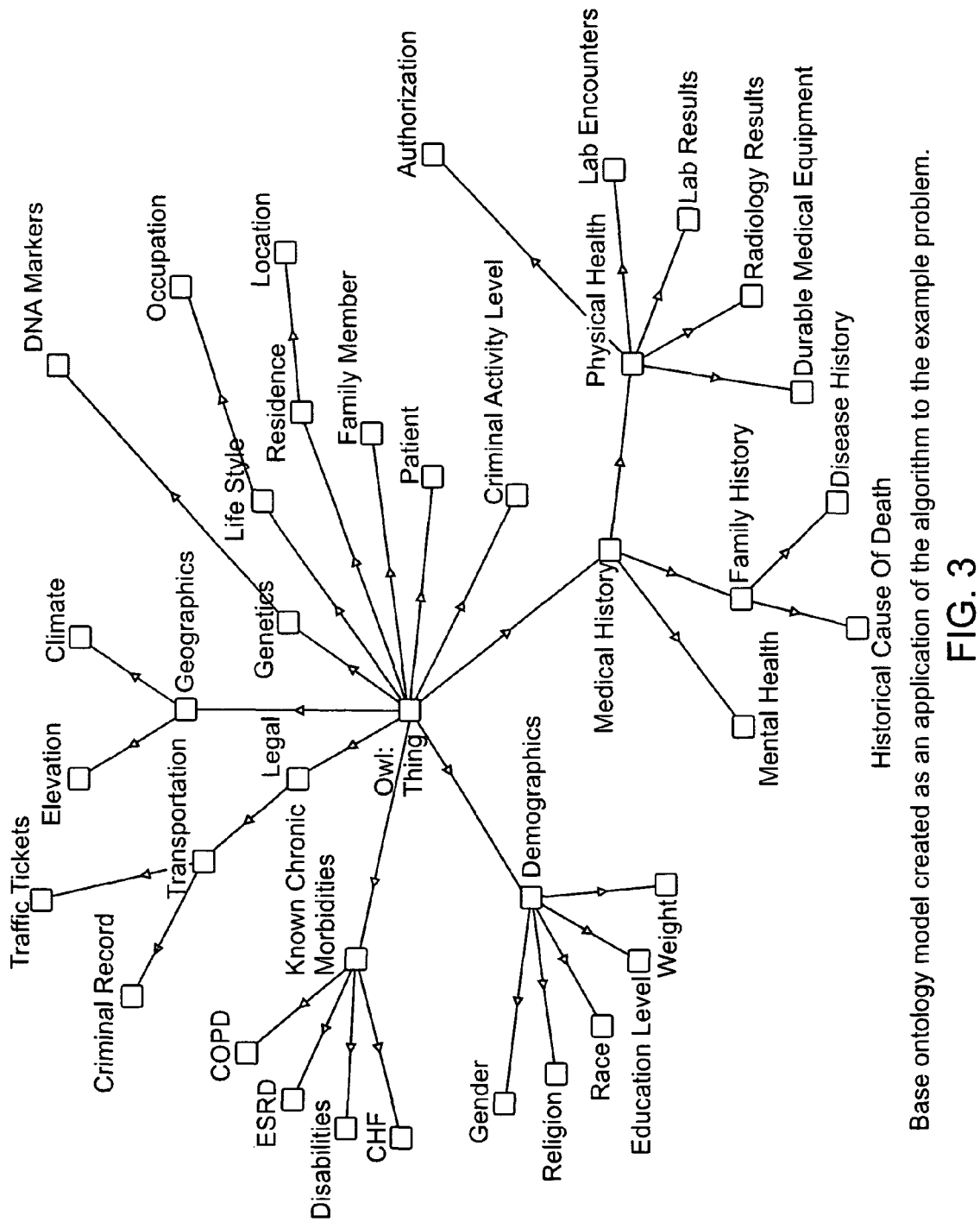
FIG. 3 is an example of a base ontology model which is created as an example for application of the present invention algorithm method to facilitate decision making in the medical risk analyses on the ICD-9 related diseases.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Traditionally healthcare providers have been trained to provide quality of care and have not had an incentive nor the training to accurately code diagnoses and procedures to a high level of specificity. The use of medical records are migrating to electronic storage and the use of the information is broadening in to areas like payment of services and care, quality of care measurements, research of population trends and patterns of disease and many other business and medical applications. The need to have medical diagnosis date coded accurately and completely continues to grow. Therefore, there is a significant need to provide algorithm methods to generate a medical utilization profile for a patient, thereby helping a decision making on cost effectiveness of the medical business.

The present invention algorithm method introduces a new and unique method of first determining risk distribution and second provide an interpolative technique for filling of the unknown risk segments in the context of diagnosis categorization. An example of application of the algorithm is to help medical organizations identify missing and mis-coded ICD-9 codes for individual patients as they are reported in their medical records regardless of the date storage model (paper or electronic). The improvement of the diagnosis coding will improve data collected and stored and will yield more accurate aggregate outcomes in decision making of the medical business for medical care providers and patients.

There are two related classifications of diseases with similar titles, and a third classification on functioning and disability. The International Classification of Diseases (ICD) is the classification used to code and classify mortality data from death certificates. The International Classification of Diseases, Clinical Modification (ICD-9-CM) is used to code and classify morbidity data from the inpatient and outpatient records, physician offices, and most National Center for Health Statistics (NCHS) surveys. Essentially, what the algorithm does is to provide a structure by which to define and quantify different types of risk given a dataset whose subset may be ICD-9, but that this subset, in and of itself, may be sufficient for the quantification process (the larger superset may provide more accurate results, but ICD-9 data alone is enough for a base-line quantification using the outlined algorithm).

Referring to Illustration 1, there is illustrated an activity diagram of a possible realization of the present invention algorithm. Included herein are the following:

Invention Algorithm:

Step 1: Defining an ontology definition to match the data sources from:
Professional encounter data
Inpatient and outpatient institutional data
Authorizations
DME Claims
Drug Claims
Lab Results
Lab Claims Success/Fail of past suspects
And Other Sources of Data for Predicting DIAGNOSIS IF CHRONIC HEALTH CONDITIONS.
Environmental data that may span across multiple patients that share environmental information such as geography, exposure to certain types of environmental elements, working conditions, etc.

Step 2: Creation of an in-memory, cached, or persistent ontology implementation that can wholly contain both characterization, classification, and instance data of a given analysis sequencer.

Step 3: Enabling the base ontology so that the predicates (edges on the graph) as well as the nodes (subjects and objects) may contains mathematical and statistical meaning so as to make possible:
Better performance through eliminating or pruning insignificant paths (statistical/mathematical derivation of significant)
Flexibility in introducing specific models each of which may suit an application better Step 4: Allowance for hierarchical comparisons or side-by-side comparisons of the ontologies through set theory so that the intersections, unions, etc. yield significant results that may drive business rules.

Step 5: The ability to apply various reasoning engines to draw inferences based on the application of the algorithmic invention as outlined below.

Alternative steps can be described as follows:
The present invention is algorithmic method for generating a medical utilization profile for a patient, comprising steps of:
1. determining medical data sources which contain medical data of said patient;
2. applying reasoning engines to define an initial ontology model which matches said data sources;
3. creating an ontology implementation that includes characterization, classification of said medical date in a given analysis sequence;
4. enabling said initial ontology model to thereby modify said initial model; and
5. comparing the initial ontology model with the modified ontology model through a Set Theory including comparing with intersections and unions which yields results to drive business rules.

The above steps can be seen realized in Illustration 1. Please note the steps do not map one-to-one to the activities in the illustration as the above steps are the algorithmic approach while the illustration is a UML Activity Diagram (similar to a process flow, etc.) which shows a higher level of detail of a possible realization of the algorithm.

The first step of the present invention algorithm method is to determine available medical data sources which contain medical date of the patient having specific diseases, for example, related the ICD-9 coded diseases. The available data sources include professional medical care institutions, inpatient and outpatient institutional records, authorizations, DME claims, drug claims, lab results, lab claims success/fail of past suspects, environmental data that may span across multiple patents that share environmental information such as geography, exposure to certain types of environmental elements and working conditions, and data specifically related to chronic health conditions.

The ICD-9 coded diseases are defined as follows. There are two related classifications of diseases with similar titles, and a third classification on functioning and disability. The International Classification of Diseases (ICD) is the classification used to code and classify mortality data from death certificates. The International Classification of Diseases, Clinical Modification (ICD-9-CM) is used to code and classify morbidity data from the inpatient and outpatient records, physician offices, and most National Center for Health Statistics (NCHS) surveys. Essentially, what the algorithm does is to provide a structure by which to define and quantify different types of risk given a data set whose subset may be ICD-9, but that this subset, in and of itself, may be sufficient for the quantification process. It will be appreciated that, the larger superset may provide more accurate results, but ICD-9 data alone is enough for a base-line quantification using the present invention algorithmic method.

The second step is to build an initial ontology model which matches the data sources, from applying reasoning engines including a device of computation, wherein the data sources are independent variables of the initial base ontology model. Referring to Illustration 3, there is illustrated a constructed base ontology model as an example of applying the present invention algorithmic method to facilitate decision making in the medical risk analysis on specific diseases, such as those related to the ICD-9 code.

Each Subject or Object in the ontology (nodes in the ontology) may be one or more independent classifiers in the ICD-9 data. It is also possible that a cluster of the Subject or Objects (nodes in the ontology) be a more granular representation of a single ICD-9 classifier. In both cases, the total set of classifiers per CDC definition of ICD-9 will always be a subset of the a cluster of subject or objects in the ontology model.

One may think of ICD-9 as a classification system for morbidity that includes their physical history. Mathematically, therefore, one may define ICD-9 as a set of variables, let's call it set Y, which is defined by its independent variables $\{X1, X2, \ldots Xn\}$ where X are the various classifications. Then, there is a mapping between Y and some grouping of the variables in the base ontology (this could be any set grouping Z where Z is defined by its independent variables $\{V1, V2, \ldots Vn\}$ where any given V is a subject or object on the base ontology).

In the context of computer and information sciences, an ontology defines a set of representational primitives with which to model a domain of knowledge or discourse. The representational primitives are typically classes (or sets), attributes (or properties), and relationships (or relations among class members). The definitions of the representational primitives include information about their meaning and constraints on their logically consistent application. In the context of database systems, ontology can be viewed as a level of abstraction of data models, analogous to hierarchical and relational models, but intended for modeling knowledge about individuals, their attributes, and their relationships to other individuals. Ontologies are typically specified in languages that allow abstraction away from data structures and implementation strategies; in practice, the languages of ontologies are closer in expressive power to first-order logic than languages used to model databases.

For this reason, ontologies are said to be at the "semantic" level, whereas database schema are models of data at the "logical" or "physical" level. Due to their independence from lower level data models, ontologies are used for integrating heterogeneous databases, enabling interoperability among disparate systems, and specifying interfaces to independent, knowledge-based services. Ontologies are also called out as an explicit layer from the technology stack of the Semantic Web standards.

The master ontology is a construction of basic triples which relate subjects and objects through predicates. Subjects and objects are nodes while predicates may be thought of as "smart edges" to connect the respective nodes of a subject and an object. Predicates do more than simply relate the subjects and objects together: they may be types, carry attributes, and be thought of as richly as nodes themselves.

Once the ontology is constructed, various statistical models, each representing one or more risk models may be applied to the ontology resulting in the association of risk attributes with the subjects, objects, or predicates. The risk model may be defined as: (1) where the collected empirical evidence is modeled by creating subjects and objects for sources of evidence (clues) of what should be documented on the qualified data and various Bayesian distributions modeling the relationships between such sources in form of attributes for the predicates; and (2) The base model itself may be thought of a risk model.

It will be appreciated that, there may be 1-N risk models. Each risk model differs from others in exact nature of:

(1) Collection and gathering of the empirical (training) date;

(2) Orthogonality (or lack thereof) of variables in the risk model;

(3) Orthogonality (or lack thereof) of variables used in measuring the empirical data for the risk model; and (4) the domain of the risk model (the perspective from which it is formed and the appropriateness to the range of types of inferences and results expected).

Each subject or object in the ontology (nodes in the ontology) may be one or more independent classifiers in the ICD-9 data, for example, the nodes of the MedicalHistory and Thing in the base ontology model which is illustrated in Illustration 3. It is also possible that a cluster of subjects or objects be a more granular representation of a single ICD-9 classifier, such as the cluster starting the node of the PhysicalHealth in the base ontology model. In both cases, the total set of classifiers per CDC definition of ICD-9 will always be a subset of the a cluster of subjects or objects in the ontology model.

One may think of ICD-9 as a classification system for morbidity that includes their physical history. Mathematically, therefore, one may define ICD-9 as a set of variables, such as a set Y, which is defined by its independent variables $\{X_1, X_2, \ldots X_n\}$ where X are the various classifications. Then, there is a mapping between the set Y and some grouping of the variables in the base ontology model, which could be any set grouping Z where Z is defined by its independent variables $\{V_1, V_2, \ldots V_n\}$. Here any given V is a subject or object on the base ontology model.

Referring to Illustration 3, the initial base ontology model contains a specific hierarchical structure, comprising various branches. The structure is comprised of nodes and predicates, where a predicate is positioned between two nodes. The hierarchical structure starts from two center nodes of Thing and MedicalHistory to develop two respective sub-hierarchical structure.

As an example of the branch which starts from the data sources of MedicalHistory containing including information related to the ICD-9 coded diseases, the data sources of MedicalHistory is defined to be a subject. The subject is through the predicate to link an object which is a data sources of MentalHealth. The MentalHealth is defined as the object since it is located at the end side of the predicate. Therefore, an object for a subject itself can be the subject, which can be illustrated through an example in the sub-hierarchical branch starting from the data source of MedicalHistory. The MedicalHistory connects to a data source of PhysicalHealth. Therefore, the PhysicalHealth is an object of the subject Medical History. However, the PhysicalHealth is the subject in accordance with relationship of a predicate to a data sources of LabResults.

The predicate is comprised of relationship between the respective subject and object. The relationship can be mathematical, or statistical or stochastic. The statistical relationship is related to the probability theory. Hereafter is an example of a statistical rule: multiplying all probabilities of triples, a patient A is relating to illness B through probability distribution $P(X)$ by $Q(X)$ distribution where patient A is in Set C representing residence in geographic area determined by some geographic boundaries.

The stochastic relationship is referred to including a probability distribution assigned to a specific risk for a specific patient sample over a period of time or a probability distribution assigned to a specific set of patients in a set A which is related to an illness B. Mathematically, the stochastic rule may be realized from the following example: if a patient A has been treated with a medicine B for time length t, then the risk of developing side-effects associated with the medicine B are $Q(P(X),t)$.

The mathematical relationship is any relationship which differs to the statistical and stochastic relationship. Therefore, the mathematical relationship includes logics. Example of a logic rule may be as follows. If a patient A has had an illness B and the illness B is treated by a medicine C, and the medicine C also treats an illness D, and the patient A is currently being treated for the illness B, then the probability of contracting the illness D is reduced by $P(X)$ which is some probability distribution.

Establishing these statistical, stochastic, or mathematical relationships among the empirical evidences of the base ontology model may use any single or combination of methods including prevalence, expert knowledge, crosswalks and coding intensity. However, these relationships may, in turn, be associated with the subjects, objects, or predicates. Therefore, the data collection process can be characterized as a process which yields relevance to the ontology construction. It is appreciated that the classification of the independent variables recognized in the first step of the present invention algorithmic method and the structure of the rule reasoner recognized through the discussion of the risk models are both orthogonal to the actual statistical, stochastic, or mathematical relationships. In other words, any statistical, stochastic, or mathematical relationships my be used in itself to draw conclusions given a set of data. However, the power of the present invention algorithmic method comes in when it is applied to.

Based on the selected risk model, a set of inferences may be drawn which can then be used to add "result nodes" (subjects or objects) to the ontology model, thereby continually evolving the ontology itself and making the inference process more accurate. Such inference may also be thought of as assertions that are added to the ontology model or modify the reasoning engine behavior dynamically so that they are not "forgotten" in future analysis, but may be included or excluded iteratively. Result nodes can be a distinct hierarchical condition categories (HCC) in the member's profile or other data elements that the system is configured to predict.

The third step of the present invention algorithmic method is to create an ontology implementation that includes characterization, classification and instance of said data organized by a given analysis sequence of said base ontology model.

The ontology implementation refers to use the reasoning engines including their hardware and software to entail associating mathematical, or stochastic, or statistic quantification of the relationships between the respective subjects and objects of the loaded instances in the initial base ontology model.

The characterization refers to find new information which has not been listed in the initial ontology model. For example, a new information is discovered after quantifying the relationship between the subject LifeStyle and the object Occupation. While LifeStyle can be considered a set of variables $\{X_1, X_2, \ldots, X_n\}$, some subset of this set may be included in ICD-9. Occupation is a set not included in ICD-9. As previously mentioned, the algorithm and the ontological technique used to analyze the data is a superset of the ICD-9 defined classifications. This is an example of where there is an intersection, but there are certainly variables falling outside of the ICD-9 problem. The new information is further determined to only associate with the subject LifeStyle. Therefore, the new information can be implemented into the existing ontology model as a new tree branch structure, subject-object, of the existing ontology model.

While LifeStyle can be considered a set of variables {X1, X2, . . . , Xn}, some subset of this set may be included in ICD-9. Occupation is a set not included in ICD-9. As previously mentioned, The algorithm and the ontological technique used to analyze the data is a superset of the ICD-9 defined classifications. This is an example of where there is an intersection, but there are certainly variables falling outside of the ICD-9 problem.

The classification refers to define existing information to appropriate classes so that they can be analyzed in accordance with various weights. While the first set of the weights can be effected by an analysis of the ICD-9 data, they are not directly dependent or related to the ICD-9 data. The weights essentially say how important is each one of the variables recognized in the ICD-9 classification based on what type of risk which will be computed.

While the first set of the weights can be effected by an analysis of the ICD-9 data, they are not directly dependent or related to the ICD-9 data. The weights essentially say how important is each one of the variables recognized in the ICD-9 classification based on what type of risk we want to compute.

The Instance refers to organized raw data so that the data may be fitted into the model". ICD-9 classifications are not the data, rather a subset of the base ontology. So, as related to this paragraph, ICD-9 data is part of the model.

The given sequence refers to orders and routes of the hierarchical structure of the initial base ontology model, while the hierarchical structure is considered as a subset structure of the ontology model.

The fourth step of the present invention is to enable the ontology model including quantifying the mathematical, statistical and stochastic relationships of the predicates between the respective nodes of the initial ontology model to thereby modify the initial ontology model.

After implementing the ontology on the initial empirical model, the predicates and nodes contain specific mathematical, stochastic and statistical meanings, so that a better performance can be achieved through eliminating or pruning insignificant paths having the respective predicates and nodes. Therefore, specific new models which each suits the better application can be conducted, which results in that the existed initial model is further improved.

The term "stochastic" within the context of the application of the algorithm may refer to one of many things, including the situation in which they are: (1) they probability distribution [P(X) over T] assigned to s specific risk for a specific patient sample over a period of time and some associated error distribution associated with such probability distribution. The error distribution may be statistical or stochastic in nature. For example, this could be the "Historical Data" which is used to build the initial set of facts in the ontology and associate some mathematical distribution with the triples (subjects and objects). The values will represent the probability distribution and the error (anomalies, inaccuracies caused by data collection, etc) may be associated with the error distribution; (2) The probability distribution assigned to a specific set of patient in set A relating to illness B where patients in set A have a common medical history over time period $\{t_1, t_2\}$ where $t_1$ is a starting time and $t_2$ is an ending time.

The fifth step of the present invention algorithmic method is to compare the initial ontology model with the modified ontology model through a Set Theory including comparing with intersections and unions, wherein the comparison yields results to drive business rules.

Set Theory is the mathematical science of the infinite. It studies properties of sets, abstract objects that pervade the whole of modern mathematics. The language of set theory, in its simplicity, is sufficiently universal to formalize all mathematical concepts and thus set theory, along with Predicate Calculus, constitutes the true Foundations of Mathematics. As a mathematical theory, Set Theory possesses a rich internal structure, and its methods serve as a powerful tool for applications in many other fields of Mathematics. Set Theory, with its emphasis on consistency and independence proofs, provides a gauge for measuring the consistency strength of various mathematical statements. There are four main directions of current research in set theory, all intertwined and all aiming at the ultimate goal of the theory: to describe the structure of the mathematical universe. They are: inner models, independence proofs, large cardinals, and descriptive set theory. See the relevant sections in what follows.

The initial empirical ontology model is compared with the improved model after implementing the ontology through a hierarchical comparison or side-by-side comparison. The hierarchical comparison refers to compare with the whole tree structure starting from the central nodes, such as the MedicalHistory and the Thing. The side by side comparison refers to first compare with each specific subject and object, for example, the LifeStyle and Occupation. This comparison can be gradually applied to every pair of the subject and object. Therefore, a weighed average can be conducted for the whole ontology model after completion of the side-by-side comparison.

During the comparison, the Set Theory is implemented so that the similar data will be compared as the union where they are consistent with each other. Data which has some similarity will be compared as the intersections where they are intercepted at specific nodes.

Results of the comparison are represented to a risk assessment of the medical records for the patient having the specific diseases, such as those related to the ICD-9 code. The risk assessment is based on a derived risk model. This risk model can be broken down to various sub risk model aligning with the various issues. All these risk models are foundation for driving the respective business rules.

Some of the advantages of the outlined algorithm and technique are as follows:

(1) Providing higher degree of flexibility in separating the base model subjects and objects (a subset of which are the ICD-9 data) from their inherent relationships and the mathematical, stochastic, and statistical nature of any particular risk analysis. This decoupling allows for not only near real-time manipulation of the risk models for massively large data sets (exceeding, for example, terabytes), but also the ability to do comparisons and simulations between different risk models which may have inherently different mathematical, stochastic, and statistical attributes which they introduce to the predicates in the ontology model;

(2) The ability to analyze data and quantify risk using ICD-9 classification (and hence data organized in such fashion) along with other classifications which may be a superset of ICD-9 classifications;

(3) The ability to identify new patterns of risk by walking through the ontology graph and applying the mathematical, stochastic, or statistical properties relevant to the predicates and hence quantify risk by walking through the nodes;

(4) The ability to provide a massively scalable infrastructure that may be deployed on grid-like computing environments for medical risk quantification;

(5) The algorithm is inherently evolutionary as it will improve itself via a control-system-like feed-back mechanism to improve the ontology; and (6) The algorithm and methodology predicates can have their own associated mathematical, stochastic, and statistical models which can be categorized. Therefore, this enables many existing actuarial and risk-analysis techniques to be applied.

It will be appreciated that a key consideration to the entire application is that the algorithm has been specialized to fit risk models applicable to healthcare where patient data has usual attributes of:

(1) Variable in time with some probabilistic distribution and some error distribution;

(2) Individual data points may or may not refer conclusions very different from the collection of such data points;

(3) The application of Ontologies, Set Theory, stochastic processes, and statistical analysis in a single model that enables an inherent weighing of the proper variables and derivation of singular conclusions from a set of dependent or independent variables; and (4) Introduction of human intervention in correcting the error distribution in a manner that does not upset statistical, stochastic or mathematical correctness in all relevant modeling and reasoning.

It will be further appreciated that risk models as applied to the present invention may be through sets in Set Theory where any given model includes a set of facts and rules created by the aforementioned process and data collection system. Two techniques may be applied to draw inferences from such risk models and the base line which comprises the raw ontology based on the empirical evidence:

(1) Set Theory may be applied to find various set operations applied between the risk model and its byproducts and some baseline, for example, finding the intersection of a given set of data points that either comprise the risk model itself or are a result of the risk model with the baseline model. Subsequent to the application of such operation, the statistical, stochastic, or deterministic models associated with the resulting model may be applied to make proper inferences or predictions; and (2) A purely mathematical approach where some set of thresholds are chosen to indicate the error range. The risk model is then comprised of boundary contribution violation of which may indicate addition or removal of fact into the reasoning model.

In addition, it is important to use initial orthogonal variable sets to build the risk model for healthcare risk adjustment. As illustrated in the risk models from the present invention, a key component of the risk model is the actual variables used in determining the ontology. Such variables can be grouped. In fact, these groups are a fundamental foundation for the superiority and uniqueness of the approach applied by the present invention. These categories may be recognized as:

(1) Historical patient data;

(2) Non-historical environmental data about the current and likely future physical surroundings of the patient; and (3) Current course of treatment and cost or benefit correlation with historical data on the patient.

It will also be appreciated that a user intervention is also important in the application of the present invention. Since one of the commercial manifestation of the algorithmic invention will be in form of a software program, the following have been recognized as human intervention points with the system, which refers to the user interface interactions:

(1) Potential manual correction/calibration of the stochastic, statistical, or mathematical quantifiers associated with the subjects, objects, or predicates of the ontology model. For example, in case of a table-driven implementation of the statistical data, numbers may be manually manipulated by a human being given known circumstances such as a given patient population;

(2) Automated process of correction/calibration of the stochastic, statistical, or mathematical quantifiers associated with the subjects, objects, or predicates of the ontology model triggered manually;

(3) The user may be able to view the ontology and all the stochastic, statistical, or mathematical quantifiers associated with the subjects, objects, or predicates of the ontology;

(4) Evaluation and interaction with a "work queue" where the user may be able to chose various risk models, apply them to the base model, simulate a set of inferences, and repeat this process indefinitely; and (5) Ability to schedule a predetermined set of interactions with the "work queue" as described in the item (4) above.

Illustration 2 demonstrates the architectural software implementation of the invention. The "Ontology" is a distributed concept between the ontology engine and the data store where the data store holds the raw information and the ontology engine is able to load such information into memory and process it. The reasoning engine, in turn, is able to interact with the ontology engine, given a set of rules which may be logical or mathematical (stochastic, statistic, etc.) rules.

Example of a logical rule may be: If patient A has had illness B, and illness B is treated by medicine C, and medicine C also treats illness D, and the patient is currently being treated for illness B, then the probability of contracting illness D is reduced by P(x) which is some probability distribution.

Example of a stochastic rule may be: If patient A has been treated with medicine B for time length t, then the risk of developing side effects associated with medicine B are Q (P(x), t).

Example of a statistical rule may be: Multiply all probabilities of triples patient A relating to illness B through probability distribution P(x) by Q(x) distribution where patient A is in Set C representing residence in geographic area determined by some geographic boundaries.

Note: Illustration 2 outlines only 3 of the independent variable stores that comprise the entirety of the data store that needs to be fed into the system.

Examples

The following example is provided for illustration of application of the present invention algorithmic method, and is not for limitation of the present invention.

Statement of Problem for Example Application:

The MMA 2003 legislation changed the way Medicare Advantage and Stand Alone Part D Plans are reimbursed for providing care to enrolled Medicare Beneficiaries. The new method is called the Risk Adjusted Payment System and uses reported ICD-9 data to CMS to calculate a health risk score. This score is multiplied with a specific plan's bid rate to determine a prospective payment to the plan.

A major problem is the collection and reporting of the diagnostic data. The plans are largely responsible for reporting the information that is documented by providers in medical records and mostly reported to plans using encounters or claims from qualified sources. The plan collects a lot of data about their members that indicate potentially missing or miscoded diagnostic information from the collected qualified data. The plan needs a method to identify what HCCs should be evidenced in the diagnostic data that are not yet reported or coded correctly by the providers.

Medicare compensates Medicare Advantage plan and Stand Alone Part D Plan using a model that pays higher monthly reimbursements for members whose health conditions are more expensive to provide professional, inpatient and outpatient and drug costs and lower for healthy members.

The basis for measuring a member's health status is based on data collected from patient medical records documented by professional, inpatient and outpatient face-to-face providers. All other sources of diagnostic or ICD-9 data is not admissible for calculating risk adjustment payments. The Medicare risk models groups ICD-9 codes in to hierarchical condition categories (HCC) who are assigned a coefficient. All of the applicable HCCs that have been evidented during a data collection period and any combination adjusters from multiple HCC interactions are summed to provide a total risk score.

Monthly payments are derived by multiplying the total risk score with the base rate in the plan's approved bid. Those members who are less healthy where the costs to provide care is higher will have a higher total risk score and receive a higher monthly payment from CMS.

Application of Algorithmic Method of the Present Invention to the Example:

The data collected for patient's medical records are used to develop models; per description of algorithmic invention, based on the stochastic, statistical, and/or known mathematical properties of the records. For example, models can be developed per patient or per patient population that share some direct attributes or correlation of attributes in their stochastic/statistical nature. Illustration 3 illustrates a model which may be considered as a canonical base model as a starting point. It must be noted that this model shows the OWL representation of the potential realization of the ontology model. The same base ontology may be represented in other forms but would convey the same meaning. The above description represents steps of collection of the medical data sources and creation of the base ontology model of the present invention algorithmic method.

Next, a software application in a device of computation, written in any variety of languages and using any desired tool sets, operating systems, etc. will be used to load the provide the ability to load the initial set of collected data into instances of the subjects, objects, and predicates of the ontology as formulated in the base model illustrated in Illustration 3. This illustrates the third step of the present invention algorithmic method.

Next, enabling the initial ontology model refers to quantify the mathematical, statistical and stochastic relationships between the respective nodes of the initial ontology model, so that their respective relationships and subject-object positions can be confirmed or changed which leads to modify the initial ontology model. The following are concrete examples of where such mathematical relationships may be extracted from:

(1) Rule node example with one result: the evidence node says that when a member has HCC 17 and HCC 45 there is a probability relationship to predict that HCC 85 is also documented in the medical record. This rule is an evidence node and HCC 85 is the result node;

(2) Crosswalk node example with multiple results: The Drug Claim data has a NDC 873456234 that maps to 3 ICD-9 codes 127.0.0.0, 85.1.0.0 and 120.1.1.0. Two of the ICD-9 codes map to two HCC categories; HCC 17 and HCC 108. Each of the relationships or edges between the evidence node and the two result nodes has a different probability to predict the HCC in the base line profile; and (3) Crosswalk node example with one result: The Authorization data has an authorization request for ICD-9 code=127.0.0.0 that crosswalks to HCC 17. This is s case where there is evidence in the Auth evidence node that HCC 17 should be in the profile with some probability.

Various operation that the algorithmic method may yield in providing business value include:

(1) Deriving inferences (conclusions) based on different models that were built using different data sources, but have some independent variables in common or have some known intersection in their dependent variables.

(2) Deriving new risk modes for high-level analysis that may not be derivable from empirical data, but are desirable to know (what-if scenarios) within some stochastic or statistical certainty.

For this example, it cold add that there is a statistical probability distribution $P(X)=\{p_1(X), p_2(X), \ldots, p_n(X)\}$ such that n is the number of predicates in the ontology above (the number of lines between the nodes) and that each relationship is then associated with such probability so that when traversing the relationships in the ontology with the reasoner so that it can also obtain some probability quantification.

For example, if assuming that there is a probability $q_1(X)$ that a member of population of a given weight range will have a disease A. In addition also assuming that there is a probability q2(X) that if a given patient has a family member with disease A, then he/she will have the disease A at some time. If the relationship in the example ontology is both transitive and symmetric (properties of the ontology are defined at ontology definition time), and a patient is in the given population and has the family member with the disease, then the probability of the patient have the disease is $W(X)=[p_1(X)*q_1(X)]+[p_2(X)*q_2(X)]$, where $p_1(X)$ and $p_2(X)$ are the probability distributions associated with the predicates in the ontology. This same concept may be extended to stochastic model where the probabilities are looked at for particular tome windows and time is considered as another variable.

The last step of the algorithmic method is applied, in this case, by taking the base model with the base date and looking at the differences between the base instance data (instance data as applied to the example ontology) and any new data set applied to the same ontology, then discovering patterns of intersections, recognizing points of zero probability, and other various calculations that will result in drawing conclusions by using the reasoner and making comparisons between different instance models, then applying such conclusions in a feed-back loop so as to improve the ontology where applicable, and finally drive the inferences that provide business value in form of risk quantification or otherwise, for example, drawing the conclusion that risk cost of medication over the letter half of an individual's life with a given disease is higher if this person has used a particular medication in the first half of the life.

Defined in detail, the present invention is an algorithmic method for generating a medical utilization profile for a patient, comprising steps of: (a) determining medical data sources which contain medical data of said patient; (b) applying reasoning engines to define an initial ontology model which matches said data sources; (c) creating an ontology implementation that includes characterization, classification of said medical date in a given analysis sequence; (d) enabling said initial ontology model to thereby modify said initial model; and (e) comparing the initial ontology model with the modified ontology model through a Set Theory including comparing with intersections and unions which yields results to drive business rules.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A computer-implemented algorithmic method for generating a medical utilization profile for a patient, comprising steps of:
  a. determining medical data sources which contain medical data of said patient;
  b. applying reasoning engines to define an initial ontology model which matches said data sources;
  c. creating an ontology implementation that includes characterization, and
classification of said medical data in a given analysis sequence;
  d. enabling said initial ontology model to thereby modify said initial model; and
  e. comparing the initial ontology model with the modified ontology model through a Set Theory including comparing with intersections and unions which yields results that drive business rules; and
  f. generating a patient profile.

2. The algorithmic method in accordance with claim 1, wherein said medical data sources are provided including initially and sub-sequentially.

3. The algorithmic method in accordance with claim 1, wherein said medical data are provided including initially and sub-sequentially.

4. The algorithmic method in accordance with claim 1, said reasoning engine including a device of computation.

5. The algorithmic method in accordance with claim 1, wherein said base ontology model includes a hierarchical structure which is of a tree structure comprising various branches having the respective nodes and predicates, said nodes are represented by the respective medical data sources, and said predicates represent the respective relationships between the respective medical data sources.

6. The algorithmic method in accordance with claim 5, wherein said nodes represent including subjects and objects.

7. The algorithmic method in accordance with claim 5, wherein said predicates represent including mathematical, statistical and stochastic relationships.

8. The algorithmic method in accordance with claim 1, wherein said base ontology model includes structure of a canonical model.

9. The algorithmic method in accordance with claim 1, further comprising that various risk models apply to said base ontology model, which results in association of risk attributes with said subjects, objects or predicates of said base ontology model.

10. The algorithmic method in accordance with claim 1, wherein said medical data sources are gathered through methods including prevalence, expert knowledge, crosswalks, and coding intensity.

11. The algorithmic method in accordance with claim 1, wherein said ontology implementation includes applying said reasoning engines to fill the initial medical data into the respective nodes of the initial ontology model.

12. The algorithmic method in accordance with claim 1, wherein said enabling includes quantifying the mathematical, statistical and stochastic relationships between the respective nodes of the initial ontology model, so that their respective relationships and subject-object positions can be confirmed or changed which leads to modify the initial ontology model.

13. The algorithmic method in accordance with claim 1, wherein said comparison includes a hierarchical comparison.

14. The algorithmic method in accordance with claim 13, wherein said hierarchical comparison starts comparing from central nodes to edge nodes of the respective entire initial and modified ontology model.

15. The algorithmic method in accordance with claim 1, wherein said comparison includes a side-by-side comparison.

16. The algorithmic method in accordance with claim 15, wherein said side-by-side comparison compares with two nodes connected by a same predicate of said initial ontology model with the respective two nodes connected by the respective same predicate of a modified ontology model, and further comparing a subsequent respective two nodes till all of nodes of the respective ontology models are compared.

17. The algorithmic method in accordance with claim 1, further comprising a feed-back loop mechanism for refining said initial base ontology model.

18. The algorithmic method in accordance with claim 1, wherein said business rule includes a decision making in medical risk analyses.

19. The algorithmic method in accordance with claim 18, wherein said risk analyses include an analysis of risk which may be generated by ICD-9 coded diseases.

20. The algorithmic method in accordance with claim 1, further comprising a mathematical convolution operation while the comparison window of the convolution, itself, could be over any area of the ontology and the convolution could be of any degree of complexity mathematically with potential stochastic and statistical properties.

* * * * *